(12) United States Patent
Tucker et al.

(10) Patent No.: US 10,173,047 B2
(45) Date of Patent: Jan. 8, 2019

(54) DEVICE FOR AUGMENTING BLOOD FLOW, TISSUE PERFUSION AND FLUID DISTRIBUTION BY NEUROMUSCULAR STIMULATION IN HORSES AND OTHER NON-HUMAN MAMMALS

(71) Applicant: Sky Medical Technology Ltd., Cheshire (GB)

(72) Inventors: Arthur Tucker, Leytonstone (GB); Duncan Bain, Kings Langley (GB); Gregory James Firth, Sheffield (GB)

(73) Assignee: Sky Medical Technology Ltd., Cheshire (GB)

( * ) Notice: Subject to any disclaimer, the term of this patent is extended or adjusted under 35 U.S.C. 154(b) by 195 days.

(21) Appl. No.: 14/410,913

(22) PCT Filed: Jun. 28, 2013

(86) PCT No.: PCT/GB2013/051718
§ 371 (c)(1),
(2) Date: Dec. 23, 2014

(87) PCT Pub. No.: WO2014/006378
PCT Pub. Date: Jan. 9, 2014

(65) Prior Publication Data
US 2015/0202427 A1    Jul. 23, 2015

(30) Foreign Application Priority Data
Jul. 2, 2012  (GB) .................................. 1211685.1

(51) Int. Cl.
*A61N 1/04* (2006.01)
*A61N 1/32* (2006.01)
(Continued)

(52) U.S. Cl.
CPC ........... *A61N 1/0452* (2013.01); *A61D 99/00* (2013.01); *A61N 1/0484* (2013.01); *A61N 1/303* (2013.01); *A61N 1/326* (2013.01); *A61N 1/36017* (2013.01)

(58) Field of Classification Search
CPC .. A61N 1/0456; A61N 1/0452; A61N 1/0492; A61N 1/04; A61N 1/36021; A61N 1/0404; A61N 1/0558
See application file for complete search history.

(56) References Cited

U.S. PATENT DOCUMENTS

| 5,487,759 A | 1/1996 | Bastyr et al. |
| 6,615,080 B1 | 9/2003 | Unsworth et al. |

(Continued)

FOREIGN PATENT DOCUMENTS

| DE | 102006030211 A1 | 1/2008 |
| GB | 2404858 A | 2/2005 |

(Continued)

OTHER PUBLICATIONS

Great Britain Office Communication dated Oct. 25, 2012 for GB Application No. GB1211685.1.
(Continued)

*Primary Examiner* — Amanda Hulbert
*Assistant Examiner* — Natasha Patel
(74) *Attorney, Agent, or Firm* — Wolf, Greenfield & Sacks, P.C.

(57) ABSTRACT

The invention relates to a method and device for neuromuscular stimulation of one or more muscles, or muscle groups, with one or more beneficial effects selected from increasing arterial, venous and capillary blood flow, increasing flux of interstitial fluid and lymphatic drainage, increasing tissue oxygenation, enhancing heat distribution, enhancing the
(Continued)

distribution of pharmaceutical products, and enhancing performance and recovery from exertion in horses.

18 Claims, 7 Drawing Sheets

(51) Int. Cl.
    *A61N 1/36*     (2006.01)
    *A61D 99/00*     (2006.01)
    *A61N 1/30*     (2006.01)

(56) References Cited

U.S. PATENT DOCUMENTS

| | | | |
|---|---|---|---|
| 9,314,609 B2* | 4/2016 | Brown | A61N 1/0452 |
| 9,333,334 B2* | 5/2016 | Jeffery | A61N 1/0492 |
| 2003/0013948 A1* | 1/2003 | Russell | A61B 5/04282 |
| | | | 600/372 |
| 2004/0065341 A1* | 4/2004 | La Fauci | A45D 8/20 |
| | | | 132/277 |
| 2007/0060975 A1* | 3/2007 | Mannheimer | A61N 1/20 |
| | | | 607/46 |
| 2009/0048642 A1* | 2/2009 | Goroszeniuk | A61N 1/36021 |
| | | | 607/46 |
| 2010/0076533 A1 | 3/2010 | Dar et al. | |
| 2010/0087903 A1* | 4/2010 | Van Herk | A61N 1/0492 |
| | | | 607/115 |
| 2012/0221014 A1* | 8/2012 | Stack | A61N 1/0558 |
| | | | 606/129 |
| 2013/0158627 A1* | 6/2013 | Gozani | A61N 1/0456 |
| | | | 607/46 |
| 2014/0238013 A1* | 8/2014 | Wu | F03G 7/06 |
| | | | 60/528 |
| 2014/0276362 A1* | 9/2014 | Alvarez | A61K 33/00 |
| | | | 604/21 |
| 2014/0277324 A1* | 9/2014 | DiUbaldi | A61N 1/0472 |
| | | | 607/139 |

FOREIGN PATENT DOCUMENTS

| | | |
|---|---|---|
| GB | 2422549 A | 8/2006 |
| GB | 2454481 A | 5/2009 |
| JP | 2011-234833 A | 11/2011 |
| WO | WO 99/64105 A1 | 12/1999 |
| WO | WO 01/03768 A1 | 1/2001 |
| WO | WO 2006/054118 A1 | 5/2006 |
| WO | WO 2010/070332 A1 | 6/2010 |

OTHER PUBLICATIONS

International Search Report and Written Opinion for International Application No. PCT/GB2013/051718 dated Oct. 15, 2013.
International Preliminary Report on Patentability for International Application No. PCT/GB2013/051718 dated Jan. 15, 2015.
Buchner et al., Physiotherapy applied to the horse: a review. Equine Vet J. Nov. 2006;38(6):574-80.
European Examination Report dated Aug. 28, 2018 in connection with European Application No. 13734143.4.

* cited by examiner

DEVICE FOR AUGMENTING BLOOD FLOW,
TISSUE PERFUSION AND FLUID
DISTRIBUTION BY NEUROMUSCULAR
STIMULATION IN HORSES AND OTHER
NON-HUMAN MAMMALS

RELATED CASE INFORMATION

This application is a 371 U.S. National Stage Application of International Application No. PCT/GB2013/051718, filed Jun. 28, 2013, which claims priority to Great Britain application no. 1211685.1, filed on Jul. 2, 2012.

FIELD OF THE INVENTION

The invention relates to a method and device for neuromuscular stimulation of one or more muscles, or muscle groups, with one or more beneficial effects selected from increasing arterial, venous and capillary blood flow, increasing flux of interstitial fluid and lymphatic drainage, increasing tissue oxygenation, enhancing heat distribution, enhancing the distribution of pharmaceutical products, and enhancing performance and recovery from exertion in horses. Aspects of the invention relate to methods of operating such a device, and to methods and apparatus for clinical application of the device in individuals affected by pathological processes and those free from disease.

BACKGROUND TO THE INVENTION

A method and device for reduction or treatment of deep vein thrombosis (DVT) are described in international patent application WO2006/054118. A method and device for reducing peripheral vascular resistance in the blood circulation of a patient are described in international patent application WO2010/070332. WO2006/054118 and WO2010/070332 are incorporated herein by reference.

WO2006/054118 relates to a device for reduction or treatment of DVT in a patient. The device is designed to be placed directly against the skin of the patient. Consequently, the electrodes of the device would not be able to penetrate through the hair of a non-human mammal to make contact with the skin. Additionally, the electrodes are not designed to engage and grip the hair and skin of a non-human mammal. Therefore, the device of WO2006/054118 is not suitable for the treatment of neuromuscular stimulation of one or more muscles, or muscle groups of a non-human mammal such as a horse.

WO2010/070332 relates to a device for preventing diastolic flow reversal in a patient. The device is designed to be placed directly against the skin of the patient. Consequently, the electrodes of the device would not be able to penetrate through the hair of a non-human mammal to make contact with the skin. Additionally, the electrodes are not designed to engage and grip the hair and skin of a non-human mammal. Therefore, the device of WO2010/070332 is not suitable for the treatment of neuromuscular stimulation of one or more muscles, or muscle groups of a non-human mammal such as a horse.

U.S. Pat. No. 6,615,080 relates to a neuromuscular electrical stimulation (NMES) device for the prevention of DVT by stimulating the musculature on the sole of the foot of a patient. The electrodes of the device, when in use, are designed to push through the material of a sock worn by a patient and consequently make contact with the skin of the patient. The electrodes are not designed to engage and grip hair of a non-human mammal. Consequently, the device would not be suitable for the treatment of neuromuscular stimulation of one or more muscles, or muscle groups of a non-human mammal such as a horse.

WO01/003768 relates to a transcutaneous electro neuro or muscular stimulation unit. The electrodes of the device are designed to be placed directly against the skin of a patient. WO99/64105 relates to a portable adjustable stimulator for preventing DVT. The electrodes of the device are designed to be placed directly against the skin of a patient and are held against the skin of the patient by a cuff or sleeve. GB 2 404 858 relates to a DVT and circulation therapy device. The electrodes of the device when in use are designed to be placed directly against the skin of the patient. US 2010/0076533 relates to a device for transmitting an electrical stimulation to a bodily tissue of a patient. The electrodes of the device when in use are designed to be placed directly against the skin of the patient. U.S. Pat. No. 5,487,759 relates to an electrical nerve and muscle stimulation and associated support device. The electrodes of the device when in use are designed to be placed directly against the skin of the patient. The electrodes of the devices of WO99/64105, GB 2 404 858, US 2010/0076533 and U.S. Pat. No. 5,487,759 would not be able to penetrate through the hair of a non-human mammal to make contact with the skin. Additionally, the electrodes are not designed to engage and grip the hair and skin of a non-human mammal. Consequently, the devices would not be suitable for the treatment of neuromuscular stimulation of one or more muscles, or muscle groups of a non-human mammal such as a horse.

GB 2 454 481 relates to a dressing with an integral electrical stimulation unit. The apparatus is designed to be placed directly against the skin of a patient for the treatment of tissue damage such as a laceration or incision. GB 2 422 549 relates to flexible electrodes comprising a honey-comb mesh designed to be placed directly against the skin for the stimulation of wound healing. The electrodes of the devices of GB 2 454 481 and GB 2 422 549 would not be able to penetrate through the hair of a non-human mammal to make contact with the skin. Additionally, the electrodes are not designed to engage and grip the hair and skin of a non-human mammal. Consequently, the device would not be suitable for the treatment of neuromuscular stimulation of one or more muscles, or muscle groups of a non-human mammal such as a horse.

The equine hoof, on contact with the ground during locomotion, dissipates the energy of impact by compression of the frog and the underlying digital cushion, and by distortion of the hoof especially at the heels. In turn, the venous plexus at the heels is compressed resulting in displacement of blood from the hoof and augmentation of perfusion within the limb. Consequently, vascular perfusion of the equine limb is enhanced by exercise and locomotion, but is reduced by restriction of locomotion and confinement. Similarly, horses that are confined to a stable frequently develop distal limb oedema, most commonly affecting the hind limbs, through relative stasis of interstitial fluid and lymphatic drainage. Under circumstances in which horses require prolonged periods of confinement due to ailments and maladies, due to the requirement for isolation, or for other reasons that result in restricted activity, these factors may have a deleterious impact on the health, welfare or performance of the horse. In particular, this will be true in clinical situations in which tissue perfusion and interstitial fluid drainage are already compromised, the requirement for 'box confinement' exacerbating this compromise with detrimental consequences for the individual.

Compromise of the flow of blood and interstitial fluid affect the rate of healing of superficial injuries and lesions in deeper structures by limiting tissue oxygenation and the transfer of cells, solutes and metabolites. This may influence the recovery from disease affecting a variety of structures including skin, muscles, tendons, ligaments and joints. In addition, in situations in which the flux of blood and interstitial fluid is compromised, delivery of veterinary pharmaceutical products and other medicinal agents from blood to tissues may be sub-optimal or inadequate. Furthermore, in horses exhibiting oedema, discomfort may be experienced, together with a reduced inclination for locomotion, resulting in further exacerbation of compromised fluid flux within tissues. These factors may have deleterious repercussions for the recovery of horses from injuries or diseases irrespective of whether confinement is a feature of their management.

It is believed that the method and device as described herein for augmenting fluid flux in and around tissues by neuromuscular stimulation will have wide ranging benefits to horses suffering clinical disease through promotion of tissue oxygenation, cell, solute and metabolite transfer, heat distribution and distribution of medicinal products. In particular, the health and welfare of horses exhibiting oedema through stasis of interstitial fluid, impaired lymphatic drainage or other mechanisms will be improved.

It is further believed that the method and device as described herein will provide beneficial effects in horses with compromised cardiovascular output due to a number of different pathological or physiological states that result in sub-optimal tissue perfusion. In particular, the compromised cardiovascular output may result from disease or physiological states involving the heart and vasculature, or other organs and systems that have an influence on cardiac output or blood flow. In addition, it may result from postural affects e.g. associated with recumbence during general anaesthesia, or it may result from the influence of medicinal products e.g. agents used for general anaesthesia.

It is further believed that the method and device as described herein will provide benefits to performance horses that are free from clinical disease. Such horses include racehorses, and horses involved in competitions at professional or amateur levels including but not limited to dressage, cross-country, show jumping, endurance and all types of harness and carriage events. These benefits can be elicited by application of the method and device to horses in transit and confined to stables prior to competition, and to horses following exertion in training or competition. In the former scenario, the flux of fluid in and around tissues will be enhanced despite restriction of locomotion, thereby limiting the physiological and metabolic consequences of confinement that otherwise might exist. In the latter scenario, augmentation of tissue perfusion and fluid flux will aid recovery of muscles from the physiological and metabolic effects of exertion. In particular, it is believed that the method and device will limit the development of delayed onset muscle soreness (DOMS) that typically occurs in the days following exertion, this being of particular significance for horses in the late stages of training prior to any competition in which optimal performance is required. Although paucity of information exists for DOMS in all species and conjecture exists regarding its mechanism of onset, including in man, it is accepted to occur in all species used for athletic activities, such as racing, and can be alleviated by neuromuscular stimulation using the method and device.

In summary, it is believed that the method and device described herein will provide benefits to horses subjected to restriction of locomotion, horses that have sustained diseases or injuries that may or may not be complicated by infection, inflammation and oedema, horses with generalised oedema due to systemic disease, and in horses with compromised general, regional or local blood flow. In addition, irrespective of the existence of concurrent disease or pathological processes, it is believed that the method and device will aid the distribution to tissues of medicinal products administered by systemic route, it will counter the adverse effect on tissue perfusion associated with certain postures, it will counter the adverse effect on tissue perfusion associated with certain medicinal products, and it will enhance competitive performance and aid recovery from exertion in horses.

It should be emphasised that the method and device, although described herein for the benefit of horses, could be used on non-human mammals of other species due to similarities in anatomy, physiology and pathology that exist between the non-human mammalian species such as a dog, cat, goat, sheep, horse and a cow.

SUMMARY OF THE INVENTION

According to the first aspect of the invention, there is provided a device for improving blood and lymphatic circulation in the limb or soft tissues in or around the axial skeleton of a non-human mammal, comprising positive and negative electrodes for administering an electrical stimulus to the limb or axial skeletal muscles of a non-human mammal; a power supply connected to the electrodes; and control means for activating the electrodes; wherein the device comprises a flexible substrate on which are mounted the electrodes, the power supply, and the control means; and wherein each electrode comprises a flexible member having engagement means which when in use engages and grips the hair and skin of a non-human mammal, such that electrical contact between the electrodes and skin of the non-human mammal is achieved.

The terms animal and non-human mammal are used interchangeably herein. The non-human mammal is preferably an animal selected from dog, cat, horse, goat, sheep, cow; most preferably a horse. We believe however that the device and methods described herein may be used generally with other non-human mammals as well.

The electrodes of the device comprise an engagement means. The engagement means can be any means of engaging and gripping the hair and skin of the animal, such that electrical contact between the electrodes and skin of the animal is achieved. It is important in certain embodiments that the electrodes not only penetrate through the hair of the animal and make contact with the skin but they are also held in place against the skin. This is achieved by the engagement means gripping both the hair and skin of the animal. A device that cannot grip the hair and skin of the animal would not be held securely in place and would be more easily displaced or removed by the animal, and may have a greater risk of failing to maintain electrical contact with the skin.

The stimulus may be applied directly to the muscles, or indirectly via stimulation of a suitable nerve. For example, in one embodiment, a favoured approach is to stimulate musculature of the pelvic limb by stimulation of the common peroneal nerve, and in another embodiment musculature of the thoracic limb is stimulated by stimulation of the radial nerve. Unless otherwise specified, it will be appreciated that all reference herein to stimulation of a limb or a muscle is intended to encompass both direct stimulation and indirect stimulation. In addition, it will be appreciated that the device may be used to stimulate any nerve and cause contraction of the respective muscle or muscles innervated by that nerve.

It will be appreciated that the reference to electrical stimulus or electrical stimuli and stimulus and stimuli are to be taken to be used interchangeably and should be understood to mean the electrical stimulation of a muscle or muscle group.

Preferably the device is used to apply an electrical stimulus to the limb of an animal or to the axial skeleton to elicit an isometric contraction of the muscles. An isometric contraction of the muscles should be understood to mean muscular contraction without muscle shortening and movement in any joint about which the muscle is attached.

The device allows contraction of limb muscles to take place even when the animal, such as a horse, is confined in a horse box for example, and so maintain effective blood flow and lymphatic flow by virtue of muscular action in the manner of a vascular pump.

The control means of the device preferably repeatedly activates the electrodes for repeatedly administering an electrical stimulus to the muscles. Conveniently the stimulus is administered repeatedly for the duration of a journey or other temporary period of immobility, or for the duration that augmentation of tissue flux is deemed desirable.

In a preferred embodiment, the device is applied to stimulate the common peroneal nerve in the pelvic limb to elicit isometric contraction of the muscles innervated by that nerve.

In another preferred embodiment, the device is applied to stimulate the radial nerve in the thoracic limb to elicit isometric contraction of the muscles innervated by that nerve.

In another embodiment, the device is applied to stimulate any peripheral nerve of the pelvic limb to elicit isometric contraction of any muscle innervated by that nerve. For the sake of clarity, any peripheral nerve can be interpreted to include all nerves and their respective branches or divisions that are derived from nerves or neurones of the lumbosacral plexus or spinal cord segments L4 to S4 including the femoral nerve, obturator nerve, cranial gluteal nerve, caudal gluteal nerve, sciatic nerve and pudendal nerve, together with additional nerves that innervate muscles of the trunk and viscera. It should be recognised that inter-species variation may exist in the precise pathway of innervation of muscles in the pelvic limb and the nomenclature used to describe the various nerves at any particular location within the limb may vary between the species.

In another embodiment the device is applied to stimulate any peripheral nerve of the thoracic limb to elicit isometric contraction of any muscle innervated by that nerve. For the sake of clarity, any peripheral nerve can be interpreted to include all nerves and their respective branches or divisions that are derived from nerves of the brachial plexus or spinal cord segments C5 to T2 including the suprascapular nerve, subscapular nerve, musculocutaneous nerve, axillary nerve, radial nerve, median nerve, and ulna nerve, together with additional nerves that innervate muscles of the trunk. It should be recognised that inter-species variation may exist in the precise pathway of innervation of muscles in the thoracic limb and the nomenclature used to describe the various nerves at any particular location within the limb may vary between the species.

In a further embodiment, the device is applied to stimulate any nerve that innervates a muscle or plurality of muscles attached to the axial skeleton such that vascular flux is augmented by virtue of the effect on vessels within or in the vicinity of the stimulated muscle.

A typical electrical stimulus may be at a current of between 0 to 100 mA, preferably 0 to 50 mA, more preferably 1 to 40 mA, and most preferably between 1 to 30 mA. Other examples of stimulus currents include between 15 and 30 mA.

The stimulus may be an AC waveform, although it is preferably a DC waveform, more preferably a pulsed DC waveform. The stimulus may have a frequency of 0.01 to 100 Hz, preferably 0.1 to 80 Hz, more preferably 0.1 to 50 Hz; and more preferably still 0.1 to 5 Hz. The most preferred frequencies are 0.5-5 Hz, 1-5 Hz, preferably 1-3 Hz; for example, 1, 2 or 3 Hz. In other embodiments, the frequency may be from 30 to 60 Hz, and more preferably 40 to 50 Hz. Alternatively, a stimulus with a frequency from 0.1 to 1 Hz, or from 0.33 to 1 Hz may be used. The precise desired frequency may depend on the purpose of the method, the desired physiological mode of action it is intended to cause, and the general physical condition, age, sex, and weight of the subject, among other factors.

It should also be understood that great care needs to be taken when providing an electrical stimulation to the limb or limbs of a horse to ensure that the stimulation is being well tolerated and not causing undue distress or discomfort.

Specific examples of preferred stimuli include 20 mA, at a frequency of 5 Hz, 30 mA at 3 Hz, and 28 mA at 1 Hz. The most preferred stimulus is believed to be 25 mA at 1 Hz. Other stimuli may of course be used.

The stimulus may be applied for a duration between 0 and 1000 ms, between 100 and 900 ms, between 250 and 750 ms, between 350 and 650 ms, or between 450 and 550 ms. In certain embodiments, the stimulus may be applied for up to 5000 ms, up to 4000 ms, up to 3000 ms, or up to 2000 ms. Other durations may be used; again this may depend on the details of the patient or the mode of action intended. Other preferred durations include from 50 to 600 ms. In certain embodiments, yet shorter durations may be used, for example from 25 µs to 800 µs.

Characteristics of the stimulus may vary over time. For example, a single stimulus may increase in current over the duration of the stimulus. Preferably the increase is gradual up to a peak; the stimulus may then either be maintained at the peak; terminate at the peak; or decrease in a gradual manner. Alternatively, where repeated stimuli are applied, characteristics of the stimuli may vary between different stimuli. For example, successive stimuli may be applied at increasing levels of current. Again, these successive stimuli may increase up to a peak gradually, followed by maintenance at that peak, or decrease from the peak. A cycle of increasing stimuli may be repeated a number of times. In another example, the pulse frequency may vary over time such that a pattern or rhythm of pulses is provided which, itself may vary over time. In preferred embodiments, each stimulus is a single pulse, rather than multiple brief pulses.

Stimuli may be applied at a plurality of locations on the muscles. For example, stimuli may be applied along the main (long) axis of the limb. Such stimuli may be applied simultaneously, or preferably sequentially such that a 'wave' of stimuli proceeds along the limb. Preferably, such a wave proceeds upward toward the body of the animal. This wave effect serves to generate a corresponding wave of muscle contraction which wave may help to promote blood flow away from the limb. However, in a preferred embodiment of the invention a stimulus is applied at a single point on the limb, for example to stimulate the common peroneal nerve, as described above. "A single point" may include stimulation by more than one electrode, for example, a pair of positive and negative electrodes, with a sufficiently small separation (for example, 10-50 mm, or up to 30 mm centre-to-centre separation) such that the stimulation is experienced at a point by the animal rather than over a larger area. Particularly good results have been obtained using a centre-to-centre separation of 70 mm; in preferred embodiments this is in combination with 25 mA, 1 Hz stimulation, with pulse widths in the range of 40 us to 112 us.

In certain embodiments one electrode substantially encloses the other electrode; preferably the positive electrode substantially encloses the negative electrode.

In certain embodiments one electrode has a greater surface area than the other electrode; preferably the positive electrode has a larger surface area than the negative electrode.

By "substantially encloses" is meant that one electrode surrounds at least 66%, preferably at least 75%, more preferably at least 85%, more preferably at least 90%, and most preferably 100% of the perimeter of the other. It is not essential that the one electrode be entirely enclosed by the other.

In some embodiments the electrodes are in the form of concentric, or substantially concentric, circles. In others, the electrodes are generally elongate, preferably generally quadrilateral, such as rectangular, or C-shaped or U-shaped.

In a preferred embodiment each electrode is formed by a flexible member possessing adhesive properties in addition to the engagement means such that each electrode is inherently capable of attachment to skin or hair. Alternatively, the attachment of each electrode to skin or hair may be facilitated by employment of a separate component or substance to achieve adhesion.

In an alternative embodiment the engagement means comprises a flexible member having a generally helical shape; preferably the flexible member is a spring and more preferably the flexible member is a compression spring. In this embodiment, the engagement means is formed by the coils of the helical shape. The engagement means in this example functions by the coils of the compression spring being flexed open and so engaging the skin through the hair. When the compression spring is allowed to close, returning to its resting state, the coils grip the skin and hair held within each coil, holding the flexible member to the animal and making electrical contact between the spring and the skin.

In another embodiment each electrode is formed by a flexible member having engagement means for penetrating the hair of the animal, such that electrical contact between the electrodes and skin is achieved. For example, the engagement means may comprise teeth. Preferably the teeth have a rounded profile. The rounded profile of each tooth is devoid of sharp edges or projections that could gouge the underlying skin. Importantly this ensures the safety of the animal when the device is in use and provides greater comfort when the device is fitted, providing a more tolerable experience for the animal. In one embodiment the flexible member comprises a spring with a flattened profile. By using springs with a flattened profile it is possible to maximise the total surface area of skin contact. It should be understood that the flattened profile is meant to mean that the spring does not form a perfect circle when viewed in cross section, instead the spring has at least one side and preferably two sides that are flattened to provide an increased surface area that can make contact with the skin. This has the benefit of increasing the surface area of the skin in contact with the flexible member, which has the effect of reducing the charge density and reducing the risk of accidental burning of the skin.

In one embodiment the engagement means, for example a spring, is bent substantially 90°. Bending the springs through 90° has the effect of opening up the coils of the spring which may promote their ability to penetrate in between the hair of the animal.

In one embodiment the engagement means comprises grooves cut into the surface of the flexible member; preferably the grooves are cut at 90° to 45° to the surface of the flexible member. The engagement means in its resting state is closed and by bending or flexing the flexible member the grooves open and can be placed against the leg. When the flexible member is released and allowed to return to its resting state the grooves close fastening onto the skin and hairs of the animal. Furthermore, in addition to gripping or holding the device in place the engagement means additionally ensures that the electrodes penetrate through the hair of the animal and make contact with the skin. This contact with the skin is essential so as to generate an isometric contraction of the muscles when the device is in use. A device that cannot grip the hair and skin of the animal would not be held securely in place and would be more easily displaced or removed by the animal. Consequently, a device that is held against an animal solely by means of an adhesive applied directly to the electrodes and the surface of the flexible substrate may not penetrate through the hair of the animal and make sufficient contact to the skin so as to cause an isometric contraction of the muscles when the device is in use.

In another embodiment the dimension of the area occupied by each electrode is 5 cm×5 cm. In a further embodiment the dimension of the area occupied by each electrode is 3 cm×2 cm. In one embodiment the dimension of the area occupied by each electrode is 2 cm×1 cm. It should be recognised that electrodes of other dimensions may be utilised.

In one embodiment the positive and negative electrodes are separated by 10 to 50 mm; preferably the positive and negative electrodes are separated by approximately 15 to 35 mm; most preferably they are separated by 20 to 30 mm. The separation provides a greater level of tolerance when the device is in place and the muscles are being stimulated. Separation is measured centre-to-centre of the electrodes. In a particularly preferred embodiment, the centre-to-centre separation is 70 mm.

Preferably the device is intended for use in conjunction with a conductive gel. The gel has the surprising effect of reducing the charge density, thereby improving the tolerance of an animal to the device. The conductive gel should be applied to the engagement means of the device. In certain embodiments, the device further comprises a conductive gel.

In another embodiment the device further comprises a conductive gel pad; preferably the conductive gel pad is a hydrogel pad. The use of the hydrogel on denuded skin has the surprising effect of reducing the charge density, thereby improving the tolerance of an animal to the device.

In a further embodiment the electrodes are directly printed into the flexible substrate.

In one embodiment of the device the flexible member can be removed from the device and reconnected as required. The flexible member being removable is a preferred feature of the device as it allows the flexible member to be washed and cleaned in between use. Constructing the device so that the flexible member can be removed allows different flexible members to be used. This has the added benefit of allowing flexible members differing in size and shape to be used for different methods of use. The different uses include adapting the engagement means for different animals. In certain embodiments, therefore, the device comprises a plurality of interchangeable flexible members.

It is plausible that the ability to vary the electrode separation and/or exchange electrodes will be beneficial if a single device is used for a number of different clinical indications or at a number of different anatomical locations. For example, under certain circumstances it may be desirable to provide a high charge density over a restricted surface area which may be achieved with small electrodes, whereas with electrodes possessing a large surface area the converse effect is achieved. In addition, under some circumstances it may be desirable to provide a restricted charge field created by electrodes in close proximity, whereas under other circumstances it may be desirable to provide a larger charge field created by electrodes with a greater distance of separation.

This may be achieved by, for example, providing a movable electrode on the device which is detachable and replaceable; or for example by having the ability to effectively shorten the flexible substrate such as by providing a loop in the substrate which may be enlarged or reduced in order to shorten or lengthen the substrate.

Where different sized flexible members are used, this should be understood to mean any variation in the length and width of the flexible member, including specific aspects of the flexible member. For example, where the flexible member is a wire mesh/hydrogel construct, the composition of the flexible member may vary, and where the flexible member is a spring the engagement means may also vary. In the embodiment where the flexible member is a spring the width of each coil may vary. The distance between each coil may also vary from one spring to another, though it should be noted that generally the distance between each coil for an individual spring will be generally the same. Therefore the engagement means can be adapted to suit the animal it is intended to be attached to.

Preferably the spring selected has a specific gap size between each coil of about 5 mm to about 50 mm.

Preferably different flexible members can each comprise a different sized engagement means. By providing flexible members with different sized engagement means it is possible to engage the skin through hair of different lengths at the time of use. This is preferable as it may not always be possible or convenient to trim the coat of the animal (for example, a horse) prior to using the device and, by providing flexible members with different engagement means, flexibility and convenience is provided for the device's use.

Preferably each electrode of the device is approximately 5 cm×5 cm or more preferably each electrode is approximately 2 cm×1 cm.

Preferably the positive and negative electrodes are separated by approximately 10 to 70 cm, more preferably the positive and negative electrodes are separated by approximately 10 to 30 mm. Even more preferably the positive and negative electrodes are separated by approximately 20 mm.

In a preferred embodiment of the device the flexible member is washable in between use; preferably the flexible member is a spring that can be washed. Ideally the spring is a compression spring.

In one embodiment the flexible member is connected to the power supply by a conductive contact; preferably the conductive contact is copper tape.

In one embodiment of the device the nerve being stimulated is the common peroneal nerve.

In another embodiment of the device the nerve being stimulated is the radial nerve.

In a further embodiment of the device the nerve being stimulated is any nerve of the thoracic or pelvic limbs, or any nerve that innervates one or more muscles connected to the axial skeleton for which there is enhancement of the flow of blood or lymph, or for which there is enhancement of tissue fluid flux, by virtue of the effect of muscle contraction on vessels within or in the vicinity of the contracting muscle.

In another embodiment the control means can be used to select a duration of activity when the device will administer an electrical impulse.

The flexible substrate is preferably a substantially elongated strip.

Preferably the flexible substrate is clear.

In one embodiment the flexible substrate has a recessed slot corresponding to the position of each electrode.

In another embodiment the flexible substrate has recessed slots corresponding to the position of each electrode.

In another embodiment of the device the flexible substrate has electrodes permanently located along the strip.

In another embodiment of the device the appropriate positioning of the device is facilitated by a flexible template through which the appropriate locations for attachment of each electrode can be identified and marked.

In one embodiment the device further comprises an attachment means for attaching the device to the animal.

In one embodiment the attachment means is an adhesive strap; preferably the attachment means is adhesive porous polyurethane foam.

In a further aspect of the invention there is provided a method of reducing or preventing oedema in the limb of a horse, the method comprising administering one or more electrical stimuli to a plurality of limb muscles sufficient to cause isometric contraction of the muscles.

In a further aspect of the invention there is provided a method of reducing or preventing lymphangitis and cellulitis in the limb of a horse, the method comprising administering one or more electrical stimuli to a plurality of limb muscles sufficient to cause isometric contraction of the muscles.

In a further aspect of the invention there is provided a method of reducing or preventing oedema, lymphangitis or cellulitis, the method comprising administering one or more electrical stimuli to a plurality of muscles attached to the axial skeleton sufficient to cause isometric contraction of the muscles.

In a further aspect of the invention there is provided a method of enhancing tissue oxygenation and the transfer of cells, solutes and metabolites in the tissues of a horse, the method comprising administering one or more electrical stimuli to a plurality of limb muscles, or muscles attached to the axial skeleton, sufficient to cause isometric contraction of the muscles.

In a further aspect of the invention there is provided a method of enhancing the distribution of pharmaceutical products or, other administered agents of natural or synthetic origin, to the tissues of a horse, the method comprising administering one or more electrical stimuli to a plurality of limb muscles, or muscles attached to the axial skeleton, sufficient to cause isometric contraction of the muscles.

In a further aspect of the invention there is provided a method of enhancing tissue perfusion by recruitment of muscles to act as vascular pumps in a horse, the method comprising administering one or more electrical stimuli to a plurality of limb muscles, or muscles attached to the axial skeleton, sufficient to cause isometric contraction of the muscles.

In a further aspect of the invention there is provided a method of improving perfusion in tissues sub-optimally or inadequately vascularised as a consequence of disease, posture or the administration of pharmaceutical products, the method comprising administering one or more electrical stimuli to a plurality of limb muscles, or muscles attached to the axial skeleton, sufficient to cause isometric contraction of the muscles.

In a further aspect of the invention there is provided a method of improving the rate or completeness of recovery from a wound, a lesion, disease or injury, the method comprising administering one or more electrical stimuli to a plurality of limb muscles, or muscles attached to the axial skeleton, sufficient to cause isometric contraction of the muscles.

In a further aspect of the invention there is provided a method of improving the performance of a horse, the method comprising administering one or more electrical stimuli to a plurality of limb muscles, or muscles attached to the axial skeleton, sufficient to cause isometric contraction of the muscles.

In a further aspect of the invention there is provided a method of improving the recovery time of a horse, the method comprising administering one or more electrical stimuli to a plurality of limb muscles, or muscles attached to the axial skeleton, sufficient to cause isometric contraction of the muscles.

In a further aspect of the invention there is provided a method of improving the recovery time of a racehorse after competing, the method comprising administering one or more electrical stimuli to a plurality of limb muscles, or muscles attached to the axial skeleton, sufficient to cause isometric contraction of the muscles.

In a further aspect of the invention there is provided a method of improving the recovery time of a competition horse after competing, the method comprising administering one or more electrical stimuli to a plurality of limb muscles, or muscles attached to the axial skeleton, sufficient to cause isometric contraction of the muscles.

In a further aspect of the invention there is provided a method of assisting in the training of a horse, the method comprising administering one or more electrical stimuli to a plurality of limb muscles, or muscles attached to the axial skeleton, sufficient to cause isometric contraction of the muscles.

In a further aspect of the invention there is provided a method of training a horse, the method comprising administering one or more electrical stimuli to a plurality of limb muscles, or muscles attached to the axial skeleton, sufficient to cause isometric contraction of the muscles.

In a further aspect of the invention there is provided a kit comprising a device comprising at least one positive electrode with engagement means; at least one negative electrode with engagement means; at least one power supply that can be connected to the electrodes; at least one flexible substrate on which the electrodes can be mounted; and at least one control means for activating the electrodes to administer an electrical stimulus to the muscle sufficient to cause the muscles to contract isometrically.

DETAILED DESCRIPTION

Figure 1A:
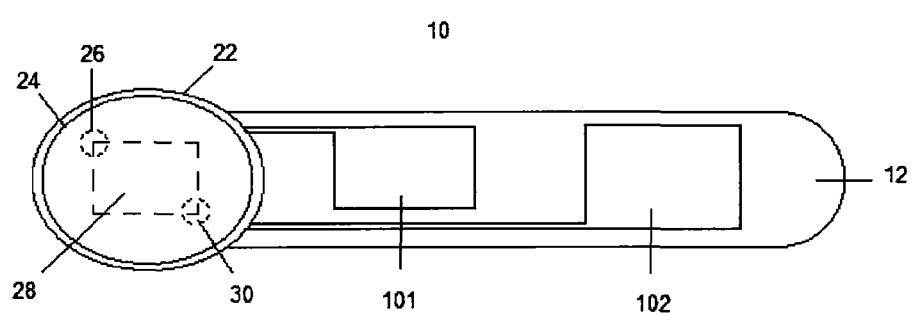
FIG. 1a shows an embodiment of a device for improving blood and lymphatic circulation in a limb of an animal.

Referring first of all to FIG. 1a, this shows an embodiment of a device for improving blood and lymphatic circulation in a limb of an animal. The device 10 includes a flexible substrate 12, having two electrodes, 101 and 102, connected to a control means 24 which includes a power cell 26, a control processor 28, and an external LED 30. The control means 24 is mounted within a cradle 22 which is integral to the flexible substrate 12.

Figure 1B:
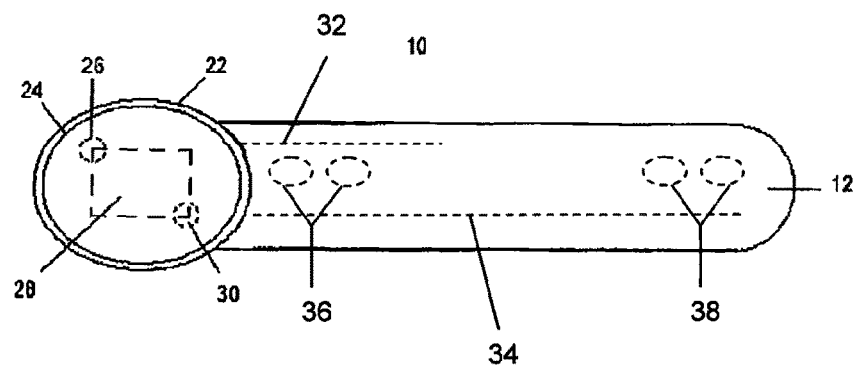
FIG. 1b shows another embodiment of a device for improving blood and lymphatic circulation in a limb of an animal.

Referring to FIG. 1b, this shows another embodiment of a device for improving blood and lymphatic circulation in a limb of an animal. The device 10 includes a flexible substrate 12, having two pairs of connecting slots 36, 38 to which electrodes can be mounted. Copper tape 32, 34 embedded within the flexible substrate connects the electrodes to the control means 24 which includes a power cell 26, a control processor 28, and an external LED 30. The control means 24 is mounted within a cradle 22 which is integral to the flexible substrate 12.

Figure 2:
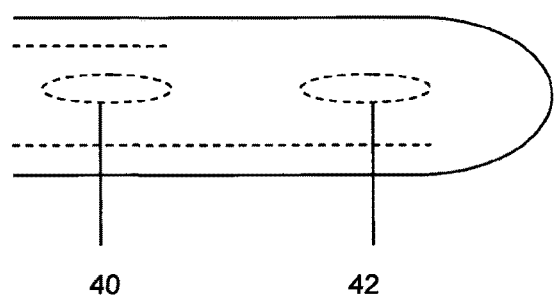
FIG. 2 shows an alternative embodiment of a device for improving blood and lymphatic circulation in a limb of an animal.

An alternate embodiment of the device illustrated in FIG. 1b is shown in FIG. 2, where the connecting slots 36, 38 are replaced by a single connecting slot per electrode 40, 42.

Figure 3:
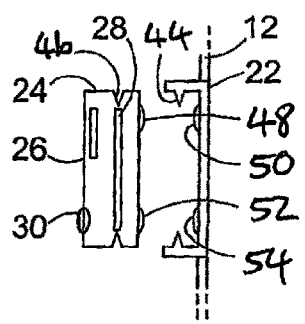
FIG. 3 shows the cradle and control module of the device.

The cradle 22 and control module 24 are shown in more detail in FIG. 3. In some embodiments, the control module 24 may be removable from the cradle 22, with a pair of detents 44 and corresponding recesses 46 allowing the cradle and control module to interlock. The control module and cradle carry corresponding electrical contact surfaces 48, 50, 52, 54 which provide for electrical communication between the control module 24 and the first and second electrodes.

Figure 4:
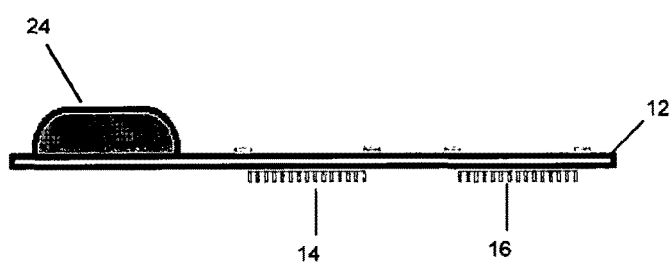
FIG. 4 shows a side profile of the device illustrated in FIGS. 1b and 2 with the electrodes 14, 16 mounted in place.
Figure 5:
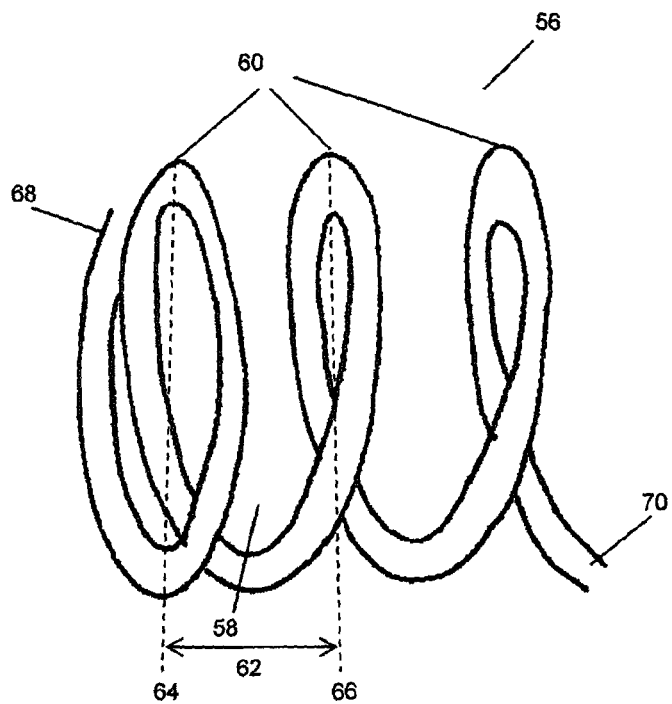
FIG. 5 shows a compression spring.

FIG. 4 shows a side profile of the device illustrated in FIGS. 1b and 2 with the electrodes 14, 16 mounted in place. In a preferred embodiment the electrodes 14, 16 are formed by a compression spring 56 (FIG. 5) with a constant gap 58 size in between each coil 60. To engage the electrodes 14, 16 with an animal the compression spring 56 is flexed opening the gap 58 between each coil 60 and placed against the skin and hair of the animal.

Figure 6:
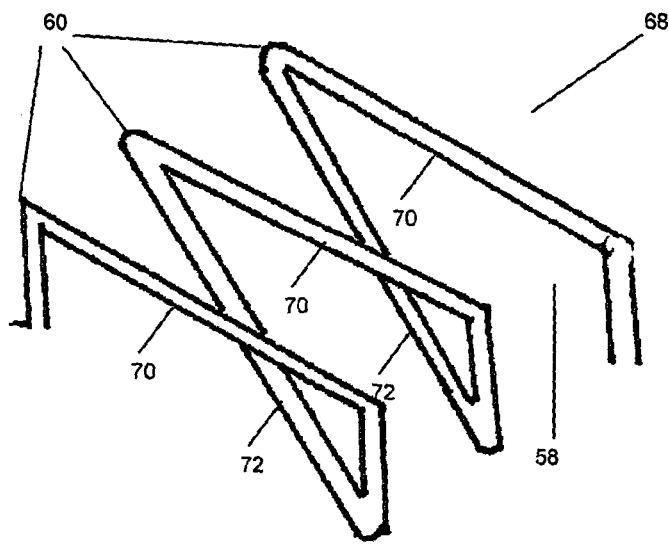
FIG. 6 shows a compression spring with a flattened profile.

In another embodiment of the device the compression springs have a flattened profile (FIG. 6). At least one surface 70, preferably two opposing surfaces 70, 72 are flattened. The flattened surfaces 70, 72 ensure that the maximum surface area of the electrode 14, 16 is in contact with the skin.

Figure 7:
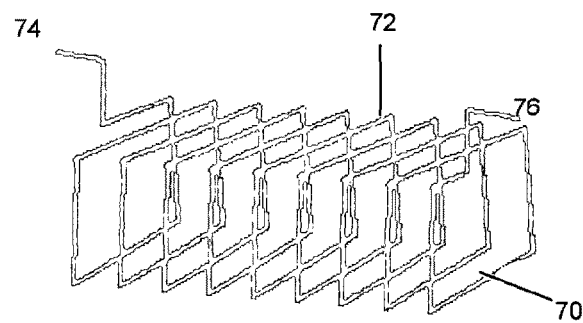
FIG. 7 shows a removable electrode with a flattened profile

In a further embodiment of the device the electrode can be removed from the device. The electrodes in this embodiment of the device further comprise a connecting means 74, 76 that engages the electrode to the device (FIG. 7). The connecting means 74, 76 of the electrode 14, 16 are designed to engage the copper tape 32, 34. By compressing the compression spring 56 enables the connecting means 74, 76 to be inserted into the connecting slot(s) 36, 38 or 40, 42. When the compression spring 56 is released it returns to its resting state pressing the connecting means 74, 76 into the connecting slot(s) 36, 38 or 40, 42. The pressure the compression spring 56 exerts engages the connecting means 74, 76 with the copper tape 32, 34.

Figure 8:
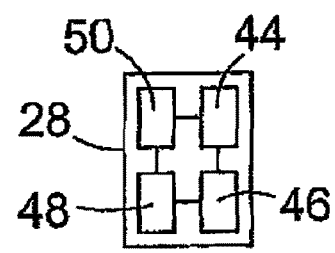
FIG. 8 shows an illustration of the control processor

A schematic illustration of the control processor 28 is shown in FIG. 8. The processor 28 includes a timer module 44, a data store 46, a program store 48, and a logic unit 50.

In use, the device is operated as follows. The flexible member 12 is attached to an animal's fore limb, hind limb or other appropriate region of anatomy, such that the first electrode 14 and the second electrode 16 are located in the vicinity of the nerve(s) and muscle(s) to be stimulated. A button is pressed to activate the device.

The program store 48 is preloaded with an operating program arranged to activate the electrodes each minute using a 40 Hz pulsed DC of 20 mA for 0.1 second. Both electrodes are activated simultaneously. The timer module 44 serves to generate appropriate timing signals, while the logic unit 50 executes the program of the program store 48.

As the electrodes 14, 16 are activated; the animal's muscles are stimulated to achieve isometric contract. Simultaneously with each activation of the electrodes, the LED 30 on the outer surface of the control module 24 is also activated; this provides a visual confirmation that the device is operating.

The control module 24 may be provided to the user in a sealed form, to be discarded when the power cell 26 is depleted. A replacement control module may then be fitted. In certain embodiments of the invention, a range of different control modules may be available, with a range of different pre-programmed patterns for activating the electrodes. A user may select a different module based on a number of different conditions (for example, animal's physical health, length of journey, size of limb of the animal, and the like). Alternatively, the control module 24 may be partly user-programmable, to allow selection of one of a number of preset programmes from a single control module.

Figure 9:
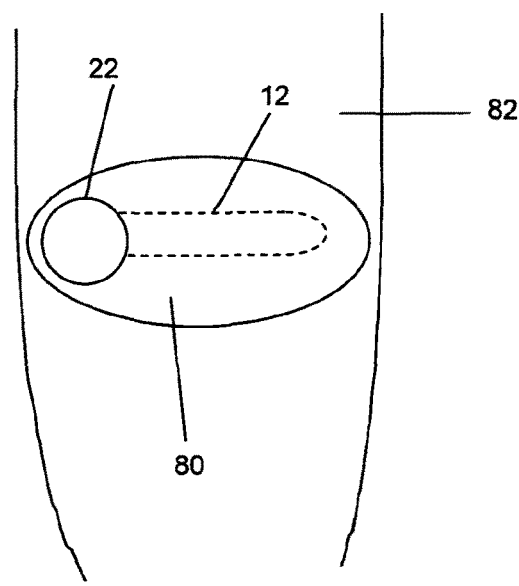
FIG. 9 shows the device embodied by FIGS. 1a and 1b held in place by adhesive porous polyurethane foam.

The device 10 in FIGS. 1*a* and 1*b* can be held in place by adhesive porous polyurethane foam such as Animal Polster 80. FIG. 9 shows the device 10 held in place by Animal Polster 80 on the hind limb 82 of a horse.

The skilled person will understand that further variations on the invention described herein are possible. For example, rather than using Animal Polster, an adhesive conductive gel could be used. Alternatively, the device may be used on denuded skin by placing the device against a gel pad such as hydrogel and holding the device in place by use of Animal Polster or another type of adhesive material.

Other variations will be apparent to the skilled person.

It is envisioned that the device can be used on one or both of the forelimbs and/or one or both of the hind limbs and/or any other appropriate anatomic region, or any combination thereof. The device preferably is used to stimulate the radial nerve in the forelimb, the common peroneal nerve in the hind limb, or any nerve innervating one or more limb muscles or muscles attached to the axial skeleton the stimulation of which enhances blood or lymphatic circulation by virtue of the effects of contraction on vessels within or around the contracting muscle.

The radial nerve emerges between the medial and long heads of the triceps muscle, rounding the caudal surface of the humerus to gain the lateral aspect of the forelimb where it detaches branches to the extensor muscles of the carpus and digit: the extensor carpi radialis, the common digital extensor, the lateral digital extensor and the ulnaris lateralis. Correct placement of the device will elicit a neuromuscular effect in the digital extensor muscles.

Figure 10:
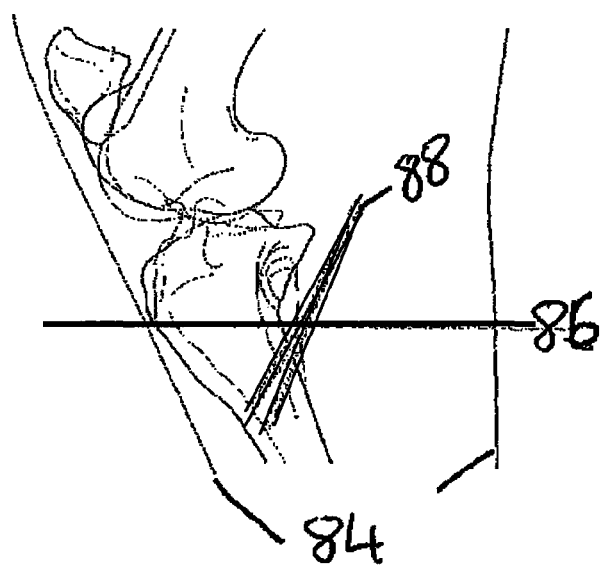
FIG. 10 shows a diagram of how to identify the position of the common peroneal nerve.

The common peroneal nerve emerges between the biceps femoris muscle and the lateral head of the gastrocnemius muscle. It divides into superficial and deep branches caudal to the lateral collateral ligament of the stifle and these branches innervate the digital extensor muscle group on the cranio-lateral aspect of the tibia. FIG. 10 shows a diagram of how to identify the position of the common peroneal nerve. The soft tissue boundaries of the leg 84 are shown around the joint with the imaginary line 86 through the tibial tuberosity and the common peroneal nerve and its branches 88.

Useful landmarks in identifying a suitable position for attachment of the device on the hind limb are the tibial tuberosity and the fibular head: the common peroneal nerve courses in a caudo-proximal to cranio-distal direction caudal to the fibula head. A bony prominence on the tibial tuberosity is easily palpated and an imaginary horizontal line from this point defines the level at which the device should be attached. Along this imaginary line the fibula is easily palpated. The peroneal nerve in the vicinity of its bifurcation lies just caudal to the fibula at this level.

The device has to be stably attached to the limb(s) of a horse, or other appropriate anatomical region, so that the device will be retained in the correct position for the duration of use. It should be observed that the lateral surface of the equine proximal crus has a fairly uniform convex curved conformation when the horse is standing squarely, but when walking the area cranial to the fibula varies considerably in its degree of curvature.

To retain the device in the correct position the device may be temporarily fixed in position. The inherent adhesive properties of the device alone may not be sufficient to hold the device in place.

The device may be held in place with adhesive tape, though it was found that use of adhesive tape is not well tolerated by horses due to the constrictive sensation that the tape creates. Alternatively, the device may be held in place with an elastic strap, though it was found that downward displacement of the elastic strap by the directional conformation of hair resulted in slippage of the device.

The use of adhesive gels produced a successful attachment of the device that was well tolerated. The device when attached by the use of an adhesive gel has the potential to be knocked and for the device to be partially or fully knocked free of the limb(s).

The use of adhesive porous polyurethane foam such as Animal Polster proved to be surprisingly effective at retaining the device in position for prolonged periods. The device was left in position for 14 hours and was held firmly in position for the duration of that time.

Animal Polster can be readily peeled away from the skin and hair of a horse despite the good adhesion. A slight residue may be left on any skin and hair to which it has been adhered. A medical grade adhesive remover which contains an emollient to prevent the skin from drying out can be purchased.

Use of the device on coarse cut hair reduced the effectiveness of the device to stimulate the radial or common peroneal nerves. Surprisingly it was found that the addition of a small amount of conductive gel to the site of electrode contact had the effect of enhancing conduction and thereby stimulating the radial or peroneal nerves. This is beneficial for horses suffering with conditions that cause tenderness and increased sensitivity in the legs as it means that minimal handling is required to prepare the device for placement. It is also of benefit to competition horses which often have specific clip patterns and the use of the device should not affect the pattern or cosmetic appearance of the animal.

Figure 11:
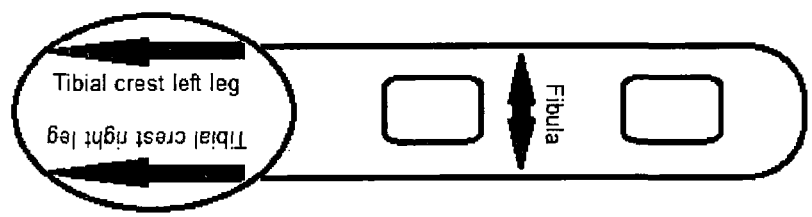
FIG. 11 shows the transparent flexible plastic template for positioning and applying the device.
Figure 12:
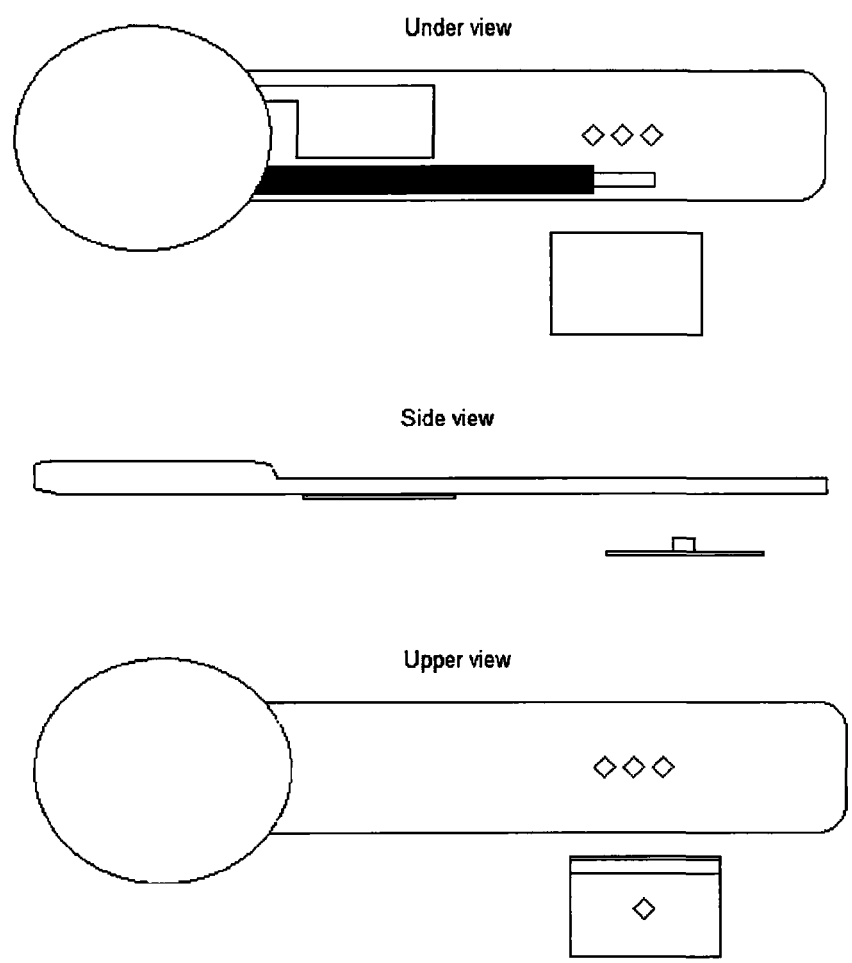
FIG. 12 shows an embodiment of the invention in which one of the electrodes is detachable and may be located in one of a plurality of positions in order to adjust the inter-electrode distance. One detachable electrode is shown, but a number of interchangeable electrodes of different sizes and shapes may be envisaged.
Figure 13:
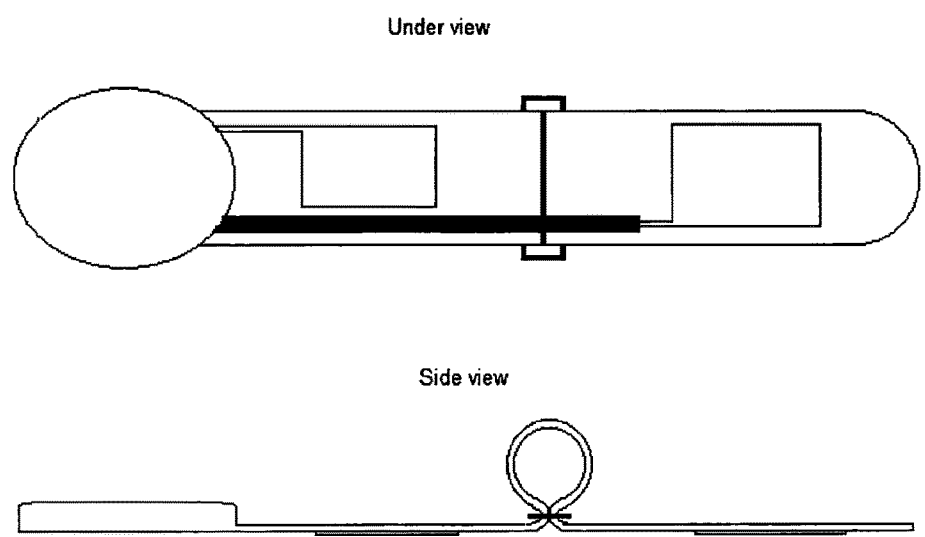
FIG. 13 shows another embodiment of the invention in which the effective inter-electrode distance may be varied by virtue of an adjustable loop in the flexible substrate which may be enlarged or reduced in size as appropriate.

It is envisioned that a transparent flexible plastic template (FIG. 11) is provided with the device. This template would be correctly aligned to the limb by referencing the bony landmarks as described. The conductive gel could be applied to the areas of the skin that would be in contact with the electrode. This application would be achieved by applying the conductive gel through holes corresponding to the position of each electrode.

Conductive coupling gel, such as ultrasound transmission gel, is a water based macromolecular gel that improves electrode/skin contact. A typical product is composed of water (90%), carbomer 940 (5%), sodium hydroxide (2%), triethanolamine (2%), antiseptic (0.5%), and edible paint (0.5%).

It is envisaged therefore that a small amount of conductive gel would be applied to bridge any gap between the skin surface and the electrodes that might exist as a consequence of the presence hair or any other obstacle impairing electrode/skin contact. The device would then be positioned in place to stimulate the target nerve. Adhesive porous polyurethane foam such as Animal Polster or Polster Plast is then placed over the device to adhere or hold the device in place for the duration of use. The device can be easily removed by peeling the adhesive porous polyurethane foam away and removing any excess adhesive from the hair or skin with a medical grade adhesive remover which contains an emollient to prevent the skin from drying out.

The device would provide a suitable method for use on horses with conditions where there is an excessive build up of interstitial fluid in the forelimb(s) or hind limb(s). Such methods of use include but are not limited to reducing or preventing oedema, lymphangitis, or cellulitis by stimulation of the common peroneal nerve, the radial nerve, or other appropriate nerves of the fore or hind limbs. The device could be used in conjunction with other methods of treatment such as physiotherapy, sessions on a horse-walker and hydrotherapy.

The device would provide a suitable method for use on horses with conditions where there is inadequacy of tissue perfusion, tissue oxygenation and distribution to tissues of pharmaceutical products or other agents. Such methods of use may be appropriate under circumstances including but are not limited to when disease or injury has been sustained or when tissue perfusion is compromised by the effects of posture or the administration of particular pharmaceutical products. The device could be used in conjunction with other methods of treatment.

The device would also provide a suitable method for limiting the vascular effects of confinement on a horse. It is envisioned that the device would be used during transportation of a horse to an event and prior to the event when the horse may be kept in confined conditions before competing.

It should be understood by reference to competitive events and competition that all levels of events are included from the professional to the amateur competing for fun. The augmentation of tissue perfusion by neuromuscular stimulation would prepare the horse for periods of potentially intense activity. The device therefore provides a method of keeping the horse in the best possible condition ahead of such periods of potentially intense activity during competition and provides a method of helping the horse achieve the best possible results during competition.

The device also provides a method for augmentation of blood and lymphatic circulation by neuromuscular stimulation of a horse when it is being stabled for any prolonged periods of time. The device could be used for example when it is not possible to allow the horse to freely roam around and thus naturally activate the musculovenous pumps of the limb. The method described therefore would be used as a prophylactic method for avoiding the excessive build up of interstitial fluid.

The device would also provide a suitable method for limiting delayed onset muscle soreness following exertion of any horse during competition, training for competition, or recreation. It is envisioned that the device would be used in this respect following physical exertion.

The life of the battery could also vary depending on its intended use. When the device is intended for use in a method to reduce the excessive interstitial fluid in cases of oedema, lymphangitis and cellulitis a long battery life ~32 hours for use in four, eight hour overnight sessions is envisioned.

For use on performance horse a device with a shorter battery life could be more appropriate and a battery life of 4 to 8 hours; preferably 6 hours, allowing a method of use to keep a horse in the best possible condition ahead of a competitive event and during the period following physical exertion.

A proof of principle study was undertaken to evaluate the vascular effects of electro-stimulation of the common peroneal nerve in three horses.

Brief Summary of the Method
- Each horse was acclimatised to room temperature for at least 30 minutes prior to collection of data.
- Hair was clipped at three sites: over the lateral femur, over the common peroneal nerve, and over the lateral aspect of the tibia distal to common peroneal nerve.
- Electrodes were attached over the common peroneal nerve, and laser Doppler fluxmetry sensors were attached at the femoral and tibial sites.
- Following acclimatisation, sequentially each horse was stimulated, allowed to rest for 15 minutes, and then walked at a constant speed for 5 minutes. Vascular flux was assessed by laser Doppler fluxmetry (Moor Instruments DRT4) at the femoral and tibial sites:
  - At rest before activation of the stimulator;
  - During stimulation of the common peroneal nerve;
  - Immediately following cessation of stimulation;
  - Immediately following cessation of walking.

Results

The laser Doppler fluxmetry output parameters recorded in this study included flux, concentration, speed and temperature.

Concentration: the concentration of red blood cells in the sampled volume of tissue. [Increase in concentration implies an increase in the volume of sampled tissue that is occupied by blood vessels, i.e. there is blood vessel dilation through engorgement of blood, and vice versa].

Speed: the speed of movement of red blood cells in the sampled volume of tissue.

Flux: the product of red blood cell concentration and speed in the sampled volume of tissue.

Temperature: the temperature recorded in the sampled volume of tissue.

1. Results (Flux)

| HORSE | Baseline value | During stimulation | Immediately post stimulation | Immediately post walking |
|---|---|---|---|---|
| MEAN FLUX DATA FROM THE LATERAL FEMUR | | | | |
| 1 | 72.3 | 171.4 | 145.4 | 125.0 |
| 2 | 210.8 | 229.3 | 206.7 | 159.0 |
| 3 | 55.6 | 165.5 | 148.5 | 124.3 |
| AVERAGE | 112.9 | 188.7 | 166.9 | 136.1 |
| MEAN FLUX DATA FROM THE LATERAL TIBIA | | | | |
| 1 | 75.3 | 110.7 | 80.1 | 93.0 |
| 2 | 85.9 | 131.6 | 84.4 | 51.8 |
| 3 | 70.3 | 112.2 | 80.2 | 90.5 |
| AVERAGE | 77.2 | 118.2 | 81.6 | 78.4 |

2. Results (Concentration)

| HORSE | Baseline value | During stimulation | Immediately post stimulation | Immediately post walking |
|---|---|---|---|---|
| CONCENTRATION DATA FROM THE LATERAL FEMUR | | | | |
| 1 | 213.1 | 231.9 | 220.8 | 295.0 |
| 2 | 212.8 | 259.4 | 196.2 | 305.6 |
| 3 | 205.4 | 226.8 | 215.3 | 295.5 |
| AVERAGE | 210.4 | 239.4 | 210.8 | 298.7 |
| CONCENTRATION DATA FROM THE LATERAL TIBIA | | | | |
| 1 | 248.7 | 420.7 | 243.4 | 411.5 |
| 2 | 244.1 | 950.7 | 238.8 | 380.3 |
| 3 | 188.1 | 463.6 | 238.2 | 416.4 |
| AVERAGE | 227.0 | 611.7 | 240.1 | 402.7 |

3. Results (Speed)

| HORSE | Baseline value | During stimulation | Immediately post stimulation | Immediately post walking |
|---|---|---|---|---|
| SPEED DATA FROM THE LATERAL FEMUR | | | | |
| 1 | 17.0 | 37.1 | 33.3 | 21.4 |
| 2 | 50.6 | 45.2 | 53.4 | 28.0 |
| 3 | 13.8 | 36.7 | 35.1 | 21.2 |
| AVERAGE | 27.1 | 39.7 | 40.6 | 23.5 |
| SPEED DATA FROM THE LATERAL TIBIA | | | | |
| 1 | 18.0 | 14.0 | 16.8 | 12.6 |
| 2 | 19.1 | 7.7 | 19.5 | 7.6 |
| 3 | 19.2 | 12.8 | 17.3 | 12.1 |
| AVERAGE | 18.8 | 11.5 | 17.9 | 10.8 |

4. Results (Temperature)

| HORSE | Baseline value | During stimulation | Immediately post stimulation | Immediately post walking |
|---|---|---|---|---|
| TEMPERATURE DATA FROM THE LATERAL FEMUR | | | | |
| 1 | 28.5 | 29.8 | 29.3 | 24.3 |
| 2 | 30.4 | 32.4 | 33.7 | 27.7 |
| 3 | 28.5 | 29.9 | 29.9 | 24.3 |
| Averaged | 29.1 | 30.7 | 31.0 | 25.4 |
| TEMPERATURE DATA FROM THE LATERAL TIBIA | | | | |
| 1 | 28.4 | 29.5 | 29.36 | 24.8 |
| 2 | 30.5 | 30.3 | 29.1 | 27.0 |
| 3 | 28.2 | 29.2 | 29.3 | 24.9 |
| Averaged | 29.0 | 29.7 | 29.3 | 25.6 |

Conclusions

Common peroneal nerve stimulation caused an increase in vascular perfusion in the equine pelvic limb and this increase was seen both proximally and distally.

Similar trends in flux, concentration, speed and tissue temperature were seen in all horses.

Over the femur, electro-stimulation caused an increase above baseline levels in mean flux of 67.2%, averaged over three horses, which persisted for an undetermined period after cessation of stimulation.

Over the tibia, electro-stimulation caused an increase above baseline levels in mean flux of 53.1%, averaged over three horses, which immediately returned to baseline levels after cessation of stimulation.

Over the femur, flux was augmented by a combination of increased concentration and increased speed.

Over the tibia, speed reduced below baseline levels during stimulation but this effect was more than offset by an increase in concentration, the overriding effect being an increase in flux. A similar fall in speed at tibial level was seen in the data collected immediately post walking. It is possible that the reduction is speed directly reflects the increase in concentration, i.e. the increase in blood vessel diameter.

Commensurate with increases in blood flow and the thermal energy dissipated by blood, electro-stimulation caused elevation in tissue temperature, this being most noticeable at femoral level. Immediately post walking, tissue temperatures below baseline levels were recorded, probably as a consequence of skin cooling via evaporative losses that occurred as a consequence of sweating (walking is an active process which provoked sweating in all horses).

Increases in concentration above baseline levels were seen over the femur and tibia on cessation of walking. This may have been a consequence of vasodilation induced by vasoactive chemicals released during homeostasis in response to an increased demand for tissue oxygenation and metabolite clearance during active exercise. This increase in concentration above baseline levels was not seen on cessation of electro-stimulation at either site, perhaps reflecting that recruitment of muscle pumps by electro-stimulation is relatively passive and without the exertion and tissue demands that accompany active exercise.

In the horse, the thoracic limbs carry a disproportionate amount of the body weight whereas the pelvic limbs contribute disproportionately to forward thrust and propulsion. Augmentation of blood flow in the pelvic limb, therefore, would be of particular benefit to racehorses and performance horses engaged in a wide range of equestrian pursuits.

However, injuries such as tendon and ligament strains most frequently affect the thoracic limb and it would be desirable to have a device that can promote healing and repair by augmenting blood flow in the thoracic limb of performance and recreational horses alike. During explorative work involving one Thoroughbred horse, successful stimulation of the radial nerve was achieved, there being concomitant visible pulsatile contraction in the innervated muscle group.

The invention claimed is:

1. A device for improving blood and lymphatic circulation in the limb or the soft tissues in or around the axial skeleton of a non-human mammal, comprising positive and negative electrodes for administering an electrical stimulus to the limb or axial skeletal muscles of a non-human mammal; a power supply connected to the electrodes; and control means for activating the electrodes; wherein the device comprises a flexible substrate on which are mounted the electrodes, the power supply, and the control means; and wherein each electrode is a generally helical spring, which when in use engages and grips the hair and skin of a non-human mammal, wherein the electrodes are maintained in contact with the mammal and wherein electrical contact is provided between the engagement means and the skin of the mammal to permit an electrical stimulus to be administered to the limb or axial skeletal muscles of the mammal through the engagement means.

2. The device according to claim 1 wherein each generally helical spring has a flat profile.

3. The device according to claim 1 wherein each generally helical spring is used in a natural resting state.

4. The device according to claim 1 further comprising a conductive gel, wherein the conductive gel is ultrasound transmission gel.

5. The device according to claim 1 wherein each generally helical spring is interchangeable.

6. The device according to claim 5 wherein each generally helical spring is replaced by inserting a connecting means on the spring into a connecting slot.

7. The device according to claim 1 wherein the each generally helical spring is washable.

8. The device according to claim 1 wherein each generally helical spring is connected to the power supply by a conductive contact.

9. The device according to claim 8 wherein the conductive contact is copper tape.

10. The device according to claim 1 wherein the control means is adapted to stimulate a nerve selected from any of: the peroneal nerve, any nerve of the hind limb that is derived from neurones of the lumbosacral plexus, the radial nerve, any nerve of the fore limb that is derived from neurones of the brachial plexus, any nerve that stimulates any muscle attached to the axial skeleton.

11. The device according to claim 1 wherein the flexible substrate is a substantially elongated strip.

12. The device according to claim 1 wherein the flexible substrate has a recessed slot corresponding to the position of each electrode.

13. The device according to claim 11 wherein the flexible substrate has electrodes placed along the elongated strip.

14. The device according to claim 1 further comprising an attachment means for securing the device to a non-human mammal.

15. The device according to claim 14 wherein the attachment means is an adhesive leg strap.

16. The device according to claim 15 wherein the attachment means is adhesive porous polyurethane foam.

17. The device according to claim 1 for use on a horse.

18. A method for:
a) reducing or preventing oedema, lymphangitis or cellulitis,
b) improving the distribution of pharmaceutical products in a non-human mammal; or improving the rate or completeness of recovery from a wound, a lesion, disease, or injury; or improving perfusion in tissues sub-optimally or inadequately vascularised as a consequence of disease, posture or the administration of pharmaceutical products; or
c) improving the performance of a horse or the recovery time of a horse or in particular a racehorse after competing or a competition horse after competing; or
d) training or assisting in the training of a horse;
the method comprising administering one or more electrical stimuli to a plurality of muscles of a non-human mammal attached to the axial skeleton or limb muscles sufficient to cause isometric contraction of the muscles of the non-human mammal and wherein the electrical stimuli are administered by a device in accordance with claim 1.

* * * * *